United States Patent [19]

Nakatsuka et al.

[11] Patent Number: 4,541,957

[45] Date of Patent: Sep. 17, 1985

[54] PROCESS FOR PREPARING IODOVINYL-ESTRADIOL

[75] Inventors: Iwao Nakatsuka, Hyogo, Japan; William Eckelman, Rockville, Md.; Waclaw J. Rzeszotarski, Washington, D.C.

[73] Assignee: The George Washington University, Washington, D.C.

[21] Appl. No.: 529,908

[22] Filed: Sep. 7, 1983

[51] Int. Cl.[4] ............... A61K 49/00; A61K 43/00; C07J 3/00

[52] U.S. Cl. ................. 260/397.2; 424/1.1; 424/9

[58] Field of Search ............ 260/397.2; 424/238, 424/1.1, 9

[56] References Cited

U.S. PATENT DOCUMENTS 4,450,149  5/1984  Kabalka et al. ............ 424/1.1

OTHER PUBLICATIONS

Hanson et al., Abstr. Pap. Am. Chem. Soc., 182, (1981), NUCL 56.
Hanson et al., From Nuclear Medicine and Biology Advances, Ed. C. Raynaud, Pergamon Press, Oxford, pp. 3200–3203.
Kabalka et al., Chem. Abst., 98, (1983), #89725j.
Hanson et al., Chem. Abst., 97, (1982), #177890a.

*Primary Examiner*—Christine M. Nucker

[57] ABSTRACT

17α-[(E)-2-Iodovinyl]-estra-1,3,5(10)-triene-3,17β-diol wherein the iodine atom is radioactive can be produced from (E)-[3-acyloxy-17β-hydroxyestra-1,3,5(10)-triene-17α-yl]vinyl dihydroxyborane in an excellent yield by iodinating the same and hydrolyzing the resulting 3-acyloxy-17α-[(E)-2-iodovinyl]-estra-1,3,5(10)-triene-17β-ol.

10 Claims, No Drawings

PROCESS FOR PREPARING IODOVINYL-ESTRADIOL

The present invention relates to a new process for preparing an iodinated steroid compound, i.e. 17α-[(E)-2-iodovinyl]-estra-1,3,5(10)-triene-3,17β-diol (hereinafter referred to as "iodovinyl-estradiol") of the formula:

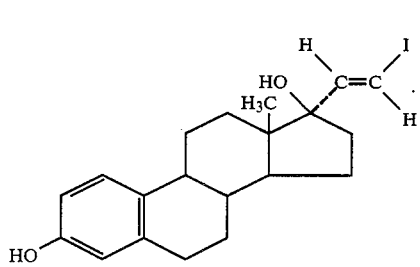

which is useful in the diagnosis or treatment of diseases such as breast cancer, prostatic cancer, uterine cancer and abnormality of estrogen receptor in human being and animals. The iodine atom in the iodinated-estradiol may be a radioactive one.

In recent years, the knowledge relating to the receptor has held an important position in physiology and pathology. It is considered that some of physiologically active substances, which have an enormously high specific activity to a living organism at an extremely small quantity, are bound to the receptor which is specific to each of the said substances at the initial stage of their reaction process. It can therefore be presumed that the receptor is changed in quantity or function in certain diseases. In fact, a number of studies have been made on the relations between various diseases and receptors.

Receptor-binding radiopharmaceuticals have been developed with these points as the background. The purpose of the said pharmaceuticals is to use in the diagnosis of the various diseases by administering them to a living organism and measuring non-invasively changes of receptors in the organism.

In order to use radiopharmaceuticals in the measurement of changes of receptors or in the diagnosis of diseases by detecting such changes, it is considered that the said pharmaceuticals have to satisfy the following requirements: (1) they must have high affinity for the receptor; (2) they must be very specific for the receptor; (3) they must have high specific radioactivity; (4) the labelled element therein must not be liberated in the living organism.

Researches have been actively done seeking for radiopharmaceuticals such as estradiol derivatives labelled with radioactive iodine which is directional to the receptors for estrogens, for use in the diagnosis of breast cancer, uterine cancer, etc., but said pharmaceuticals which satisfy the above requirement have not been found out for a long time.

Recently, it has been reported by R. N. Hanson et al. that the radioactive iodovinyl-estradiol satisfies the said requirements (American Chemical Society Meeting, August, 23-28, 1981. reference NUCL 56). According to Kabalka et al., the radioactive iodovinyl-estradiol can be prepared by the following process (Applications of Nuclear and Radiochemistry, Lambrecht RM, Morcos N, Eds. Newark, New Jersey, Pergamon Press, Chap. 17):

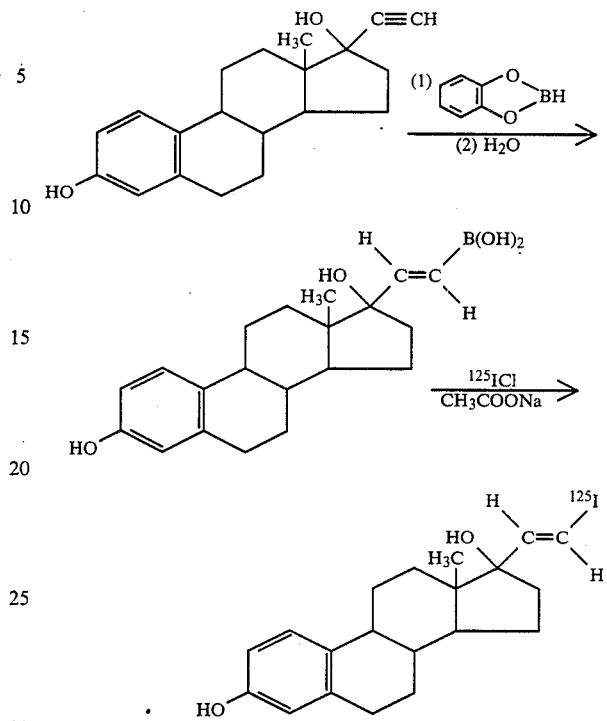

Since a quantity of the receptor in an organ is considered to be only from $10^{-9}$ to $10^{-7}$ mol concentration, the receptor-binding radiopharmaceuticals must have a very high specific radioactivity to use in the measurement of accumulation at the affected part by means of the imaging method or the probe method. On the other hand, the reexamination of the said Kabalka et al. process revealed that the radioactive iodovinyl-estradiol is obtainable only in a very low yield, i.e. less than 5% based on the radioactive iodine, and in a less pure state.

According to the present invention, there is provided a new process for preparing the iodovinyl-estradiol, particularly the radioactive iodovinyl-estradiol having an excellent specific radioactivity in a high yield. Thus, the iodovinyl-estradiol, which may be radioactive, can be obtained in a yield of more than 80%, and the radioactive iodovinyl-estradiol having a specific radioactivity as high as 500 Ci/mmol is obtainable. These excellent specific radioactivity and high yield are attained in the present invention by the use of the 3-acyloxy compound as the starting material for iodination.

The process of the invention is shown in the following reaction scheme:

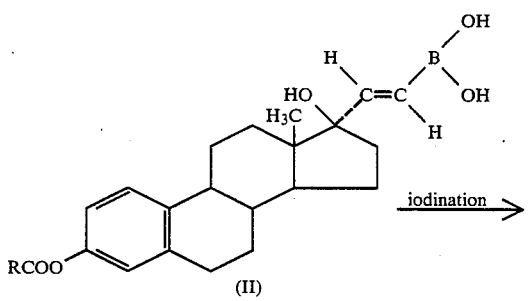

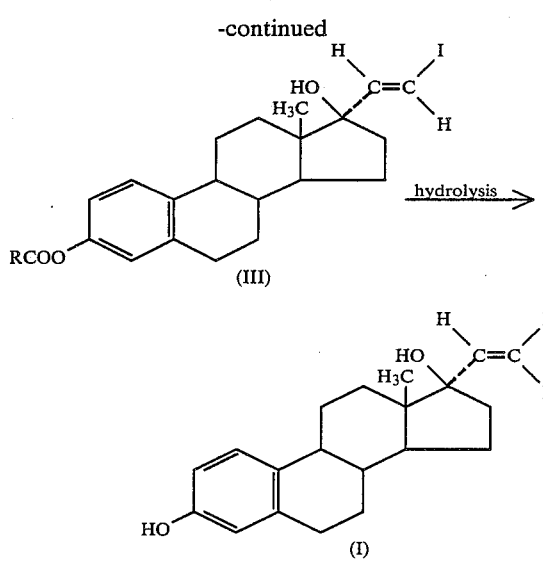

wherein R is a lower alkyl group having 1 to 4 carbon atoms, and I may be radioactive or non-radioactive. Examples of said lower alkyl group include methyl, ethyl, n-propyl, isopropyl, n-butyl, isobutyl, sec-butyl and tert-butyl.

(E)-[3-Acyloxy-17β-hydroxyestra-1,3,5(10)-triene-17α-yl]vinyl dihydroxyborane (II) as the starting compound can be prepared by reacting 17α-ethynyl-estra-1,3,5(10)-triene-3,17β-diol (i.e. 17β-ethynyl-estradiol) with catecholborane and then acylating the resultant (E)-[3,17β-dihydroxy-estra-1,3,5(10)-triene-17α-yl]vinyl dihydroxyborane with an acylating agent.

The objective iodovinyl-estradiol (I) can be prepared by iodinating (E)-[3-acyloxy-17β-hydroxyestra-1,3,5(10)-triene-17α-yl]vinyl dihydroxyborane (II) and hydrolyzing the resultant 3-acyloxy-17α-[(E)-2-iodovinyl]-estra-1,3,5(10)-triene-17β-ol (III).

The iodination may be achieved by the reaction with an iodinating agent which produces I⁻ion such as an alkali metal iodide (e.g. sodium iodide, potassium iodide, lithium iodide). In the iodinating agent, the iodine atom may be a radioactive one such as $^{125}$I, $^{131}$I, $^{132}$I or most preferably $^{123}$I. The reaction is usually carried out in a conventional solvent which does not adversely influence the reaction such as tetrahydrofuran, dioxane, methanol, water, etc. or a mixture thereof, preferably in the presence of the alkali metal salt of N-chloro-p-toluenesulfonamide such as the sodium salt of N-chloro-p-toluenesulfonamide (Chloramin T), under a mild condition.

Hydrolysis is preferably carried out in the presence of a base (e.g. sodium carbonate, potassium carbonate, sodium acetate, potassium acetate), usually in a conventional solvent which does not adversely influence the reaction such as water, methanol, ethanol, dioxane, tetrahydrofuran, ether, etc. or a mixture thereof, under a mild condition.

Since the radioactive iodovinyl estradiol obtained by the present invention has an excellent specific radioactivity, location or range of focus and degree of disease can be diagnosed easily and exactly by its administration through intravenous route to a patient and measurement of its incorporation into a specific organ by the scintigram or probe method. Thus, the radioactive iodovinyl-estradiol can be used for the diagnosis of breast cancer, prostatic cancer, uterine cancer and other diseases caused by a change of the estrogen receptor. In addition, the radioactive iodovinyl-estradiol is useful in radiologic diagnosis utilizing the difference in radioparency caused by its accumulation. For radiologic administration, it is preferable to use the radioactive iodovinyl-estradiol in an amount sufficient to gather the necessary information, which minimizes the exposure to radiant ray. In general, 0.1 to 10 ml of the solution containing 0.1 to 10 mCi of radioactivity may be administered.

The following examples are given for the purpose of illustrating the present invention.

EXAMPLE 1

(E)-[3,17β-Dihydroxyestra-1,3,5(10)-triene-17α-yl]vinyl dihydroxyborane

A mixture of 17α-ethynyl estradiol (3 g, 10 mmol, obtained commercially) and catecholborane (5 ml, 47 mmol) was heated at 70° C. for 2 hours under a nitrogen atmosphere. Water (120 ml) was added dropwise to the mixture, which was stirred overnight. The crystals formed were collected by filtration and washed with water to give 3.2 g (yield: 94%) of the desired compound. M.P. >300° C.

$^1$H NMR (60 MHz, DMSO—d$_6$) δ ppm: 0.85 (s, 3H, —CH$_3$), 1.00–3.00 (broad m, steroid nucleus), 5.42 (d, J=17Hz, 1H, =CHB(OH)$_2$), 6.30–7.2 (m, 4H, aromatic ring and —CH—).

Anal. Calcd. for C$_{20}$H$_{27}$O$_4$B (%): C, 70.19; H, 7.95; B, 3.16. Found: C, 70.11; H, 7.95; B, 3.27.

EXAMPLE 2

(E)-[3-(Acetoxy-17β-hydroxyestra-1,3,5(10)-triene-17α-yl]vinyl dihydroxyborane

A mixture of (E)-[3,17β-dihydroxyestra-1,3,5(10)-triene-17α-yl]vinyl dihydroxyborane (1 g, 2.9 mmol), acetic anhydride (5 ml) and anhydrous pyridine (7 ml) was stirred overnight at an ambient temperature. Then, the mixture was poured into ice-water. The precipitates formed were collected by filtration, washed with water and dried to give the desired acetate. The crude acetate was purified by column chromatography (silica gel, methylene chloride-methanol=95/5) to give pure acetate (yield: 60%), M.P., 215°–217° C.

IR (KBr) cm$^{-1}$: 3300, 2900, 1740, 1625, 1350, 1200, 1000.

$^1$H NMR (60 MHz, DMSO—D$_6$) δ ppm: 0.83 (s, 3H, —CH$_3$), 1.00–3.00 (broad m, steroid nucleus), 2.20 (s, 3H, —COCH$_3$), 5.38 (d, J=17Hz, 1H, =CHB(OH)$_2$), 6.35–7.60 (m, 4H, aromatic ring and —CH=).

Mass spectrum (CI, using NH$_3$) m/e: 3.40 (M+H−45).

Anal. Calcd. for C$_{22}$H$_{29}$O$_5$B (%): 68.76; H, 7.61; B, 2.81. Found: C, 68.56; H, 7.78; B, 2.67.

EXAMPLE 3

3-Acetoxy-17α-[(E)-2-iodovinyl]-estra-1,3,5(10)-triene-17β-ol

To a mixture of (E)-[3-acetoxy-17β-hydroxyestra-1,3,5(10)-triene-17α-yl]vinyl dihydroxyborane (500 mg, 13 mmol), tetrahydrofuran (5 ml), 0.066 M phosphate buffer (pH=7, 5 ml) and 1 M sodium iodide (1.13 ml, 1.3 mmol) was added chloramine T (366 mg, 1.3 mmol), and the mixture was stirred at an ambient temperature for 2 hours. Then, the reaction mixture was poured into water and extracted with ether. The ether extracts were washed with 5% sodium thiosulfate, dried over sodium sulfate and evaporated to give crude product, which was purified by column chromatography (silica gel, petroleum ether-methylene chloride=7/3) giving the desired compound (300 mg, yield: 50%). M.P., 105°–107° C. (decomp.).

IR (KBr) cm$^{-1}$: 3500, 2920, 1745, 1370, 1200, 1010, 940.

$^1$H NMR (60 MHz, —CH$_3$) $\delta$ ppm: 0.95 (s, 3H, —CH$_3$), 1.00–3.00 (broad m, steroid nucleus), 2.26 (s, 3H, —COCH$_3$), 6.21 (d, J=14.4Hz, aromatic ring).

Mass spectrum (CI, using NH$_3$) m/e: 467 (MH$^+$), 466 (M$^+$).

Anal. Calcd. for C$_{22}$H$_{27}$O$_3$I (%): C, 56.66; H, 5.84; I, 27.21. Found: C, 56.98; H, 5.45; I, 26.98.

EXAMPLE 4

17$\alpha$-[(E)-2-Iodovinyl]-estra-1,3,5(10)-triene-3,17$\beta$-diol

A mixture of 3-acetoxy-17$\alpha$-[(E)-2-iodovinyl]-estra-1,3,5(10)-triene-17$\beta$-ol (200 mg, 0.43 mmol), 1 M methanolic sodium acetate (1.3 ml), methanol (0.7 ml), 5% sodium carbonate (0.7 ml) and ether (1.3 ml) was stirred at an ambient temperature for 3 hours. The reaction mixture was poured into water and extracted with ether. The ether extracts were washed with water, dried over sodium sulfate and evaporated. The remained residue was submitted to column chromatography (silica gel, petroleum ether-methylene chloride=6/4) and then recrystallized from ethanol-water to give needles of the desired compound, M.P. 113°–115° C. (decomp.).

IR (KBr) cm$^{-1}$: 3500 3280, 2900, 1610, 1450, 1230, 1000, 950.

Mass spectrum (EI) m/e: 424 (M$^+$), 406, 391, 298, 254, 172, 159.

$^1$H NMR (DMSO-d$_6$) $\delta$ ppm: 0.77 (s, 3H, —CH$_3$), 1.00–3.00 (broad m, steroid nucleus), 6.10 (d, J=14.4Hz, 1H, =CHI), 6.70 (d, J=14.4Hz, 1H, —CH=), 6.25–7.10 (m, 3H, aromatic ring).

UV $\lambda_{max}$ (ethanol) nm (E): 280 (1780), 220 (14500).

$^{13}$C NMR (DMSO-d$_6$) $\delta$ppm: 14.0 (C$_{18}$), 22.9 (C$_{15}$), 26.0 (C$_{11}$), 27.1 (C$_7$), 29.2 (C$_6$), 32.3 (C$_{16}$), 35.4 (C$_{12}$), 39.3 (C$_8$), 43.2 (C$_9$), 46.7 (C$_{13}$), 48.6 (C$_{14}$), 74.3 (C$_{21}$), 85.8 (C$_{17}$), 112.7 (C$_2$), 114.9 (C$_4$), 125.9 (C$_1$), 130.3 (C$_{10}$), 13.7.1 (C$_5$), 152.0 (C$_{20}$), 154.9 (C$_3$).

Anal. Calcd. for C$_{20}$H$_{25}$O$_2$I.3/2H$_2$O (%): C, 53.22; H, 6.25; I, 28.12. Found: C, 53.06; H, 6.03; I, 28.35.

EXAMPLE 5

3-Acetoxy-17$\alpha$-[(E)-2-($^{125}$I)iodovinyl]-estra-1,3,5(10)-triene-17$\beta$-ol To a mixture of (E)-[3-acetoxy-17$\beta$-hydroxyestra-1,3,5(10)-triene-17$\alpha$-yl]vinyl dihydroxyborane (5 mg, 0.013 mmol), sodium ($^{125}$I)iodide (6 mCi, 0.0027 $\mu$mol), 0.06 M phosphate buffer (pH=7, 50 $\mu$l) and tetrahydrofuran (120 $\mu$l) was added chloramine T (1.13 mg, 0.004 mmol). The mixture was stirred overnight at an ambient temperature. The reaction mixture was injected into a HPLC system (column packing: Lichrosorb RP-18, 10 mm×250 mm; mobile phase: methanol-water=85/15 v/v; flow rate: 3 ml/min). The fractions were taken in a fraction collector (3 ml/min). The major fractions were combined and evaporated to give the desired compound (yield: 85%).

TLC Rf: 0.42 (solvent A: methylene chloride-methanol=99/1); 0.31 (solvent B: petroleum ether-methanol-ethyl acetate=25/3.5/3.5).

HPLC (at the same conditions as above): retention time: 16 min.

EXAMPLE 6

17$\alpha$-[(E)-2-($^{125}$I)Iodovinyl]-estra-1,3,5(10)-triene-3,17$\beta$-diol

A mixture of 3-acetoxy-17$\alpha$-[(E)-2-($^{125}$I)iodovinyl]estra-1,3,5(10)-triene-17$\beta$-ol (2.4 mCi), 1 M methanolic sodium acetate (0.4 ml), 5% sodium carbonate (0.2 ml) and ether (0.4 ml) was stirred at an ambient temperature for 2 hours. When the reaction was completed, the mixture was diluted with water (0.5 ml) and extracted with ether (2 ml×2). The ether extract was washed with water (0.5 ml) and evaporated under nitrogen stream. The residue was taken up in methanol and injected into a HPLC system (column packing: Lichrosorb RP-18, 10 mm×250 mm; mobile phase: methanol-water=77.5/22.5 v/v; flow rate: 2 ml/min). The fractions were taken in a fraction collector (2 ml/min). The procedure was repeated. The major fractions were combined and evaporated to give the desired compound (2.3 mCi, 95%), which was identical with the compound obtained in Example 4 in the following analytical data:

HPLC (at the same conditions as above): retention time: 27 min.

TLC (silica gel) Rf: 0.15 (solvent A); 0.13 (solvent B).

Specific radioactivity (measured according to radiotracer technique): 500 Ci/mmol.

EXAMPLE 7

17$\alpha$-[(E)-2-($^{123}$I)Iodovinyl]-estra-1,3,5(10)-triene-3,17$\beta$-diol

The procedures of Examples 5 and 6 were repeated except that the compounds containing $^{123}$I were used in place of the compounds containing $^{125}$I to give the desired compound, which was identified by HPLC and TLC in the same manner as that of Example 6.

Specific radioactivity: 600 Ci/mmol.

What is claimed is:

1. A process for preparing 17$\alpha$-[(E)-2-iodovinyl]-estra-1,3,5(10)-triene-3,17$\beta$-diol of the formula:

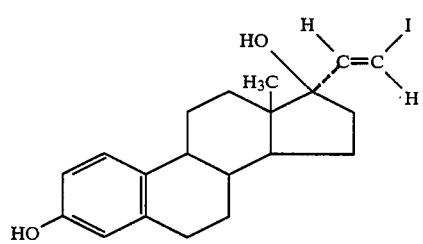

which comprises iodinating (E)-[3-acyloxy-17$\beta$-hydroxyestra-1,3,5(10)-triene-17$\alpha$-yl]vinyl dihydroxyborane of the formula:

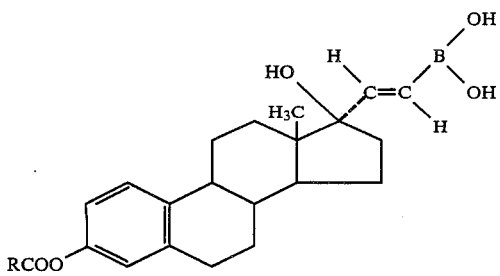

wherein R is lower alkyl group having 1 to 4 carbon atoms, and hydrolyzing the resultant 3-acyloxy-17α-[(E)-2-iodovinyl]-estra-1,3,5(10)-triene-17β-ol of the formula:

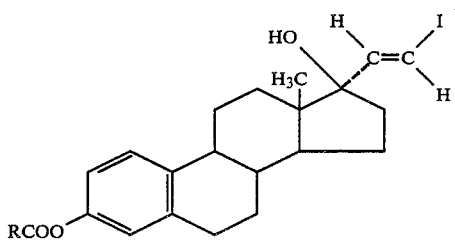

wherein R is as defined above.

2. The process according to claim 1, wherein said iodinating is carried out in the presence of an alkali metal salt of N-chloro-p-toluenesulfonamide.

3. The process according to claim 1, wherein said iodinating is carried out using a iodinating agent wherein the iodine atom is a radioactive one chosen from a group consisting of $^{123}I$, $^{125}I$, $^{131}I$, and $^{132}I$.

4. A compound selected from the group consisting of 3-acyloxy-17α-[(E)-2-iodovinyl]-estra-1,3,5(10)-triene-17β-ol, 3-lower alkanoyloxy-17α-[(E)-2-iodovinyl]-estra-1,3,5(10)-triene-17β-ol, 3-acetoxy-17α-[(E)-2-iodovinyl]-estra-1,3,5(10)-triene-17β-ol and the corresponding compounds wherein the iodine atom is radioactive.

5. The compound of claim 4 which is 3-acyloxy-17α-[(E)-2-iodovinyl]-estra-1,3,5(10)-triene-17β-ol.

6. The compound of claim 4 which is 3-lower alkanoyloxy-17α-[(E)-2-iodovinyl]-estra-1,3,5(10)-triene-17β-ol.

7. The compound of claim 4 which is 3-acetoxy-17α-[(E)-2-iodovinyl]-estra-1,3,5(10)-triene-17β-ol.

8. The compound of claim 4 which is 3-acyloxy-17α-[(E)-2-iodovinyl]-estra-1,3,5(10)-triene-17β-ol wherein the iodine atom is radioactive.

9. The compound of claim 4 which is 3-lower alkanoyloxy-17α-[(E)-2-iodovinyl]-estra-1,3,5(10)-triene-17β-ol wherein the iodine atom is radioactive.

10. The compound of claim 4 which is 3-acetoxy-17α-[(E)-2-iodovinyl]-estra-1,3,5(10)-triene-17β-ol wherein the iodine atom is radioactive.

* * * * *